US011510620B2

(12) United States Patent
Matsumura et al.

(10) Patent No.: US 11,510,620 B2
(45) Date of Patent: Nov. 29, 2022

(54) SENSOR DEVICES HAVING WEAKENED PORTIONS AND METHODS FOR USING SAME

(71) Applicant: NIHON KOHDEN CORPORATION, Tokyo (JP)

(72) Inventors: Fumiyuki Matsumura, Tokorozawa (JP); Hirohiko Ikeya, Tokorozawa (JP); Norihito Konno, Tokorozawa (JP); Jun Sakai, Tokorozawa (JP)

(73) Assignee: Nihon Kohden Corporation, Tokyo (JP)

( * ) Notice: Subject to any disclaimer, the term of this patent is extended or adjusted under 35 U.S.C. 154(b) by 985 days.

(21) Appl. No.: 15/809,743

(22) Filed: Nov. 10, 2017

(65) Prior Publication Data
US 2018/0125426 A1 May 10, 2018

(30) Foreign Application Priority Data
Nov. 10, 2016 (JP) .............................. JP2016-220013

(51) Int. Cl.
*A61B 5/00* (2006.01)

(52) U.S. Cl.
CPC .......... *A61B 5/6832* (2013.01); *A61B 5/0015* (2013.01); *A61B 5/6833* (2013.01); *A61B 5/0002* (2013.01); *A61B 2560/0214* (2013.01); *A61B 2560/0412* (2013.01); *A61B 2560/0443* (2013.01)

(58) Field of Classification Search
CPC ................ A61B 2560/0412; A61B 2560/0443
See application file for complete search history.

(56) References Cited

U.S. PATENT DOCUMENTS

| 5,936,525 A * | 8/1999 | Leyden | G08B 13/1445 340/568.2 |
| 6,112,107 A * | 8/2000 | Hannula | A61B 5/14552 600/310 |
| 2013/0116533 A1* | 5/2013 | Lian | A61B 5/35 600/391 |
| 2013/0267790 A1* | 10/2013 | Pfuetzner | A61B 5/6832 600/300 |
| 2013/0317333 A1* | 11/2013 | Yang | A61B 5/00 600/372 |
| 2015/0150505 A1* | 6/2015 | Kaskoun | A61B 5/6833 600/300 |
| 2016/0183875 A1* | 6/2016 | Yang | A61B 5/02055 600/391 |
| 2017/0015152 A1* | 1/2017 | Hartmann | B60C 23/0493 |
| 2017/0106183 A1* | 4/2017 | Silver | A61N 1/39044 |

(Continued)

FOREIGN PATENT DOCUMENTS

JP 2015520655 A 7/2015

*Primary Examiner* — Joseph M Dietrich
*Assistant Examiner* — Michael T. Holtzclaw
(74) *Attorney, Agent, or Firm* — Dorsey & Whitney LLP

(57) ABSTRACT

Examples described herein include sensor devices for measuring a parameter of a user. The sensor devices may include a reusable portion (e.g., a sensor). The sensor devices may include one or more weakened portions that may fracture on removal of a portion of the sensor device from the user. Fracturing the weakened portions may expose the reusable portion (e.g., the sensor). Accordingly, the reusable portion may be more readily observed and collected for reuse.

20 Claims, 10 Drawing Sheets

(56) References Cited

U.S. PATENT DOCUMENTS

2017/0112451 A1* 4/2017 Meyerson ............ A61B 5/0205
2017/0281073 A1* 10/2017 Drennan ................ A61F 13/02
2018/0125387 A1* 5/2018 Hadley .............. A61B 5/04085

* cited by examiner

SENSOR DEVICES HAVING WEAKENED PORTIONS AND METHODS FOR USING SAME

CROSS-REFERENCE TO RELATED APPLICATION(S)

This application claims priority to JP Application No. 2016-220013, filed Nov. 10, 2016, which is incorporated herein by reference, in its entirety, for any purpose.

TECHNICAL FIELD

Examples of sensor devices, such as those used in medical sites, are described herein which may be adhered to patients and used to measure parameters (e.g., biological signals) of the patient. In some examples, a portion of the sensor device may be reused, and the reusable portion may be readily identified.

BACKGROUND

Wearable sensors, such as used in medical sites, may include a disposable portion and a reusable portion. The reusable portion may include, for example, more expensive components and/or components which may not be as contaminated by a patient during use as the disposable portion.

SUMMARY

Examples of sensor devices are described herein. An example sensor device may include a substrate, adhesive positioned to adhere the substrate to a user, and a sensor configured to measure a parameter of a user. The sensor may be supported by the substrate, and the substrate, the adhesive, or combinations thereof, may include weakened portions configured to fracture responsive to a removal force and expose the sensor.

In some examples, the sensor device may further include a housing coupled to the substrate, and the housing may at least partially enclosing the sensor.

In some examples, the weakened portions are formed at positions corresponding to three sides of a rectangle enclosing the sensor.

In some examples, the weakened portions at least partially define a first portion of the adhesive configured to remain attached to the user following application of the removal force and a second portion of the adhesive configured to detach from the user following application of the removal force.

In some examples, the adhesive in the first adhesive area has a higher adhesive force than the adhesive in the second adhesive area. In some examples, the weakened portions are positioned at a location based at least in part on a boundary between the first adhesive area and the second adhesive area.

In some examples, the weakened portions may include at least one perforated line.

In some examples, the weakened portions have a color different than a color of a remaining portion of the substrate.

In some examples, the sensor further comprises at least one processor configured to receive signals from a sensing element and process the signals to provide at least one measurement result. In some examples, the sensor further comprises a memory configured to store the at least one measurement result. In some examples, the sensor device may further include a transmitter configured to transmit the at least one measurement result stored in the memory to a remote device.

Examples of substrate systems are described herein. An example substrate system may include a substrate and a connector at least partially supported by the substrate, the connector configured to receive a sensor, the sensor configured to measure a parameter of the user. The substrate may include weakened portions configured to fracture responsive to a removal force, and wherein the weakened portions at least partially define a first portion of the substrate configured to remain attached to the user following application of the removal force and a second portion of the substrate configured to detach from the user following application of the removal force.

In some examples, the weakened portions are formed at positions corresponding to three sides of a rectangle enclosing the connector.

In some examples, the adhesive comprises a first adhesive area corresponding to the first portion of the substrate and a second adhesive area corresponding to the second portion of the substrate. The adhesive in the first adhesive area may have a higher adhesive force than the adhesive in the second adhesive area. In some examples, the weakened portions are positioned at a location based at least in part on a boundary between the first adhesive area and the second adhesive area.

Examples of methods are described herein. An example method may include adhering a sensor device to the patient. The sensor device may include weakened portions at least partially defining a first portion of the sensor device and a second portion of the sensor device. The method may include measuring at least one parameter of the patient with the sensor device, and applying a removal force to the sensor device, the removal force configured to fracture the sensor device at the weakened portions and at least partially remove the first portion of the sensor device from the patient.

In some examples, the removal force may be further configured to at least partially remove the first portion of the sensor device from the patient while retaining the second portion of the sensor device adhered to the patient.

In some examples, applying the removal force may include peeling at least a portion of the sensor device away from the patient.

In some examples, measuring at least one parameter may include transmitting a signal indicative of the at least one parameter from the sensor device to a remote device.

In some examples, the removal force may be a first removal force. The method may further include applying a second removal force to the sensor device, the second removal force configured to remove the second portion of the sensor device from the patient, wherein the second removal force is greater than the first removal force.

DETAILED DESCRIPTION

The reusable portion of existing sensor devices (e.g., wearable sensors) may be obscured from view and it may be difficult to recognize that the reusable portion can be taken out separately from the disposable portion.

Furthermore, medical sites may make use of multiple types of sensor devices. It may be difficult for a user (e.g., nurse, aide, patient) to identify whether a particular sensor device is one that contains a reusable portion. Accordingly, reusable portions of sensor devices are currently being inadvertently discarded with the disposable portions of the sensors.

Examples of sensor devices described herein may allow a user to more readily recognize that a portion of the sensor device is reusable and can be removed from the sensor device and reused.

Figure 1:
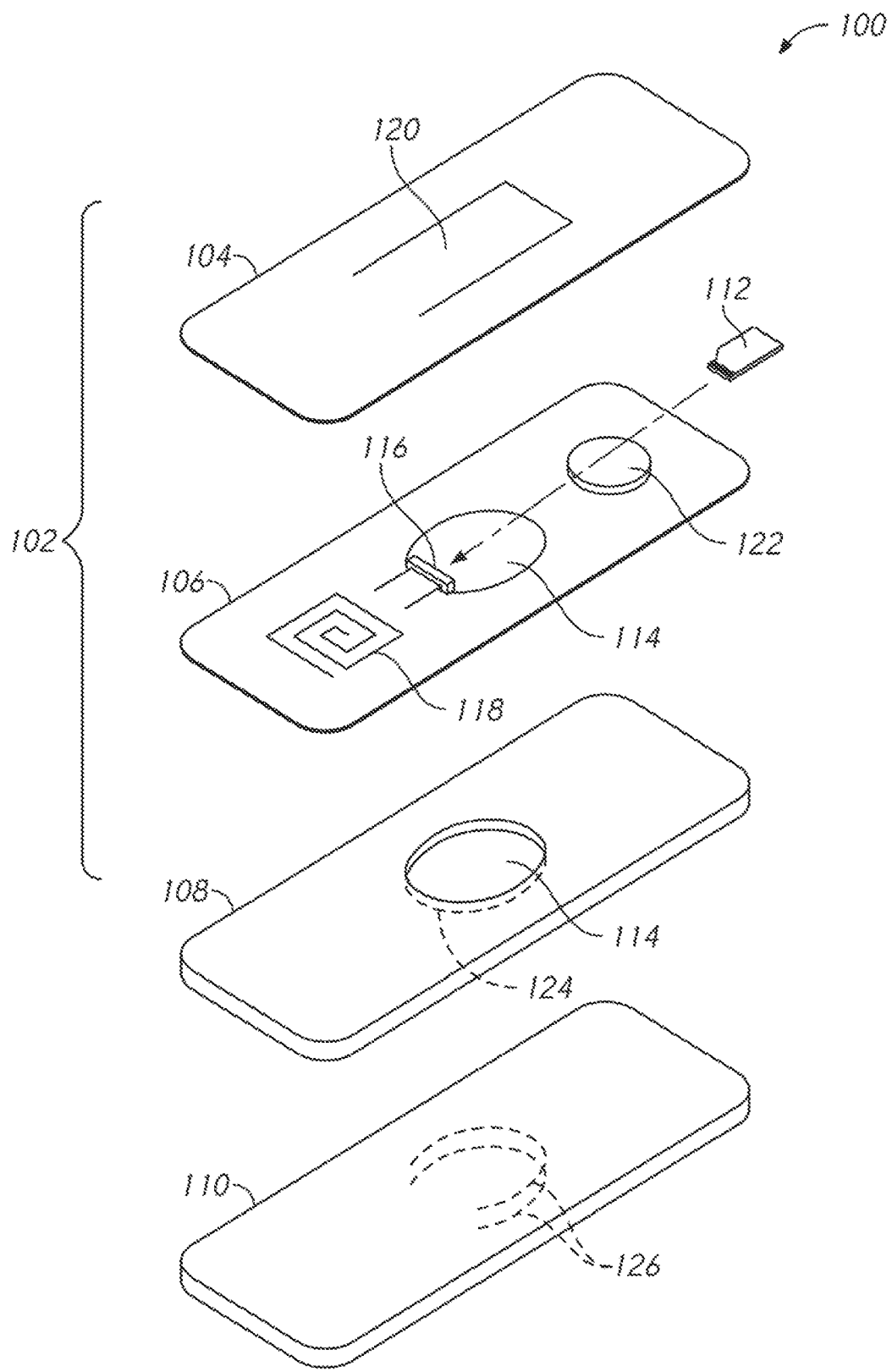
FIG. 1 is a schematic illustration of an exploded view of a sensor device arranged in accordance with examples described herein.

FIG. 1 is a schematic illustration of an exploded view of a sensor device arranged in accordance with examples described herein. The sensor device 100 includes substrate 102, adhesive 110, sensor 112, housing 114, connector 116, antenna 118, lid 120, power source 122, weakened portion 124, and weakened portion 126. The substrate 102 may be a multi-layer structure including layer 104, layer 106, and layer 108. Additional, fewer, and/or different components may be included in other examples.

Generally, sensor devices described herein, such as sensor device 100 of FIG. 1, may be attached to a user (e.g., a patient) during operation and may be portable. For example, sensor devices may be directly attached to a surface of biological tissue (e.g., skin of a chest, wrist, arm, forehead, etc.). The sensor device may be removable from the patient when a time of measurement is completed. Portions of the sensor device 100 may be disposable (e.g., substrate 102 and/or adhesive 110). Portions of the sensor device 100 may be reusable (e.g., sensor 112). The sensor device 100 may advantageously facilitate recognition that a portion of the sensor device 100 is reusable (e.g., sensor 112).

Examples of sensor devices described herein may include a substrate, such as substrate 102 of FIG. 1. The substrate 102 may be attached to a user (e.g., to a surface of a body of the user, such as skin of the user). For example, the substrate 102 may be attached to a user using adhesive 110. The substrate 102 may be disposable, and may be disposed of after a period of use. The substrate 102 may be implemented using a variety of materials. Example materials include those which may be readily attached to biological tissue surfaces (e.g., skin). Example materials may advantageously allow for housing 114 to be formed, at least in part, by the substrate 102. Example materials may advantageously have elasticity. Example materials include rubber, plastic, and/or polymer materials. The substrate 102 as shown has a rounded rectangular shape in plan view. Other shapes may be used, including but not limited to, a rectangular shape with right-angle corners, an elliptical shape, and/or a square shape.

The substrate 102 may be a multi-layer structure including layer 104, layer 106, and layer 108. The layer 104, layer 106, and layer 108 may be stacked and adhered and/or bonded together in some examples. The layer 104 may include lid 120. The layer 106 may include antenna 118, connector 116, housing 114, and power source 122. The layer 108 may include a portion of housing 114 and weakened portion 124. Other layer structures and allocation of components to layers may be used in other examples. Other examples of substrate 102 may not utilize stacked layers, or the same number of stacked layers as shown in FIG. 1. Various implementations of substrate 102 may be used. Generally, the substrate 102 may have a thickness suitable for at least partially defining housing 114. In some examples, a unitary thick piece of substrate may be used.

Examples of sensor devices described herein may include an adhesive, such as adhesive 110 of FIG. 1. The adhesive 110 may be positioned to adhere the substrate 102 to a user. The adhesive 110 may be provided on one side of the substrate 102 and may be disposed between the substrate 102 and a surface of a user (e.g., skin of a user). The adhesive 110 may exert an adhesive force with a surface of a user (e.g., skin of a user) during use sufficient to generally maintain attachment between the surface of the user and the sensor device 100 during a measurement time. The adhesive force provided by the adhesive 110 may be sufficiently small to allow the adhesive 110 to be at least partially peeled off from the surface of the user when a removal force is applied to the sensor device 100. A variety of adhesives may be used to implement adhesive 110, including, but not limited to, bonding agents.

In some examples, one or more electrodes (not shown in FIG. 1) may be disposed in the adhesive 110 and may be arranged to contact the surface of the user. The electrodes may be used to acquire a signal (e.g., a biopotential) from the surface of the user. Accordingly, in some examples, the adhesive 110 may be an electrically insulating adhesive. In some examples, a plurality of electrodes (e.g., 2, 3, 4, 5, 6, 7, 8, or another number of electrodes) may be provided at least partially in adhesive 110 and positioned to contact the surface of the user. For example, two electrodes may be provided and may be used to acquire a signal from the surface of the user and/or from an environment of the user. Electrodes provided in the adhesive 110 may be in electrical communication with sensor 112 when sensor 112 is positioned in connector 116. For example, conductive traces may be provided in substrate 102 and/or adhesive 110 that may couple the electrodes to the connector 116. In other examples, the electrodes in adhesive 110 may be capacitively coupled or otherwise electrically connected to the connector 116 and/or sensor 112.

In some examples, the adhesive 110 may be wholly and/or partially formed of an adhesive having electric conductivity (e.g., a conductive and/or partially conductive adhesive). In this manner, the adhesive 110 itself, or portions thereof, may be utilized as electrodes used to acquire signals from the surface of the user and/or environment around the user.

In some examples, prior to use, a protective sheet (e.g., release paper) may be provided on an undersurface of the adhesive 110. The protective sheet may reduce and/or prevent contamination of the adhesive 110 before using the sensor device 100. The protective sheet may be removed prior to adhering the adhesive 110 to a surface of the user in some examples.

Examples of sensor devices described herein may include a sensor, such as sensor 112 of FIG. 1. Generally, the sensor 112 refers to a reusable portion of the sensor device 100. The sensor 112 may include electronics which may be used to collect, process, analyze, and/or otherwise manipulate electronic signals to generate a measurement of a parameter of a user (e.g., a biological measurement related to the user and/or a measurement of an environment proximate the user). The sensor 112 may be supported by the substrate 102. For example, the sensor 112 may be connected to the connector 116 and/or partially housed in connector 116 and/or housing 114 during use.

Examples of sensor devices described herein may include a housing, such as housing 114 of FIG. 1. The housing 114 may be positioned and/or sized to at least partially enclose a reusable portion of the sensor device, such as a sensor (e.g., sensor 112 of FIG. 1). The housing 114 may be at least partially defined by the substrate 102. For example, a cut-out, void, or other space at least partially defined by the substrate 102 may be used to implement housing 114. In other examples, another material may be used to implement housing 114. Generally, the housing 114 may have a volume which may be larger than the sensor 112. Generally, the housing 114 may have a longitudinal dimension that may be smaller than the substrate 102 in a longitudinal direction of the substrate 102 (e.g., the housing 114 may have a length less than a length of the substrate 102). The housing 114 may be formed within the substrate 102.

The housing 114 may have a variety of shapes. In FIG. 1, the housing 114 is illustrated as having a circular shape in plan view, however, other shapes are possible. Generally, a shape of the housing 114 in a plan view may be a two-dimensional planar shape which may at least partially define a space which may enclose a reusable portion of the sensor device (e.g., sensor 112). Shapes which may be used include oval, rectangular, and/or square shapes.

Examples of sensor devices described herein may include a connector 116, such as connector 116 of FIG. 1. The connector may be implemented, for example, using a socket. The connector 116 may enclose and/or connect to at least a portion of a reusable portion of the sensor device 100 (e.g., sensor 112). The sensor 112 may, for example, be inserted into connector 116. The connector 116 may electrically connect the sensor 112 to other portions of the sensor device 100 (e.g., the substrate 102, the antenna 118 and/or power source 122). The connector 116 may be positioned on and/or within the substrate 102 to position the sensor 112 within the housing 114. Accordingly, the connector 116 may be provided at an edge of the housing 114 and/or wholly or partially within the housing 114 in some examples.

The connector 116 may be implemented using a variety of structures suitable for partially enclosing and/or electrically connecting with sensor 112. The connector 116 may include a frame into which the sensor 112 may be fitted and in which a cut-out portion may be provided for taking out the sensor 112 by a finger or the like when the sensor 112 is exposed from the sensor device 100. The connector 116 may be formed in a shape, for example, in which one side of a rectangular sensor 112 may be fitted into a socket and three sides of the sensor 112 not inserted thereto may be positioned in the housing 114. One or more electrodes may be provided by the connector 116 which may electrically connect to electrodes and/or other conductive areas of the sensor 112 to establish an electrical connection between the connector 116 and the sensor 112.

Examples of sensor devices described herein may include an antenna 118, such as antenna 118 of FIG. 1. The antenna 118 may generally be used as all or a portion of a transmitter which may transmit measurement results from the sensor device 100 to a remote device. The measurement results may be generated wholly or partially by the sensor 112. The sensor device 100 may transmit measurement results to any of a variety of remote devices in accordance with examples described herein including, but not limited to, one or more computers, servers, laptops, desktops, tablets, mobile phones, monitoring stations, or combinations thereof. Any form of wireless communication may be used, including Wi-Fi, Bluetooth, etc.

Examples of sensor devices described herein may include a lid 120, such as lid 120 of FIG. 1. Generally, the lid 120 may at least partially cover an opening in the substrate 102, e.g., in layer 104, which may be positioned at least partially over housing 114. The lid 120 may facilitate attaching a reusable portion of the sensor device 100 (e.g., sensor 112) to the substrate 102 using connector 116. The lid 120 may be implemented using a protruding opening in plan view in which three sides of a rectangle are cut (e.g., a flap). For example, the lid 120 may be implemented by cutting three sides of a rectangle in the layer 104. The lid 120 may be implemented using a flap of the layer 104 such that the flap is positioned at least partially over the housing 114 and/or connector 116 to allow a view of housing 114 and/or connector 116 when the flap is at least partially opened. The lid 120 may have an area which may larger than an area of the housing 114 in plan view. The lid 120 may be formed of a same material as substrate 102 in some examples, including but not limited to rubber.

Examples of sensor devices described herein may include a power source, such as power source 122 of FIG. 1. The power source 122 may supply power to all or portions of the sensor device 100. In some examples, the power source 122 may provide power to the sensor 112 when the sensor 112 is connected to the connector 116. The power source 122 may be implemented using, for example, one or more batteries and/or energy harvesting circuitry, including, but not limited to, energy harvesting circuitry for harvesting energy from solar, vibrational, thermal, and/or other environmental energy sources. In some examples, the power source 122 may not supply all power needs of the sensor device 100. For example, the sensor 112 itself may include a power source in some examples which may power all or some components of the sensor 112 and/or sensor device 100.

Examples of sensor devices described herein may include weakened portions, such as weakened portion 124 and weakened portion 126 of FIG. 1. The weakened portions may be fractured when a removal force is applied to the sensor device 100 to peel the sensor device 100 off a surface of the user. The fracturing of the weakened portions responsive to the removal force may expose the sensor 112. For example, the sensor 112 may increase in visibility following fracture of weakened portion 124 and/or weakened portion 126. This may allow an observer (e.g., the patient, a nurse, a doctor, or another medical professional or caretaker) to readily observe that a portion of the sensor device 100 (e.g., the sensor 112) may be reused. Accordingly, the observer may recover the reusable portion (e.g., the sensor 112) and disposal of the reusable portion may be reduced and/or avoided, particularly inadvertent disposal.

The weakened portion 124 may be formed in the substrate 102. The weakened portion 126 may be formed in the adhesive 110. Accordingly, weakened portions may be provided in a substrate, in an adhesive, or in combinations thereof in various examples. Generally, weakened portions may be provided at locations corresponding to a location of the housing 114. Weakened portion 124 and weakened portion 126 are provided generally below a location where sensor 112 is housed in the housing 114, which may allow the sensor 112 and/or housing 114 to be visually exposed following fracture of weakened portion 124 and/or weakened portion 126. Weakened portions may be provided in a position overlapping with a contour of a housing in plan view in some examples. Weakened portions may be provided in a position proximate to (e.g., in the vicinity of) a contour of a housing in some examples. The weakened portion 124 in the layer 108 may be formed on a side of the substrate 102 adjacent the adhesive 110 (e.g. a bottom and/or back surface of the substrate 102).

The weakened portions may define at least two portions of the substrate 102 and/or at least two portions of the adhesive 110. For example, weakened portion 126 may at least partially define two portions of the adhesive 110. One portion (e.g., an area generally outside of the circular contour shown in FIG. 1) may be removed from a user responsive to a removal force. Another portion (e.g., an area generally within the circular contour shown in FIG. 2) may remain attached to the user responsive to the removal force. The remaining portion of adhesive may facilitate recognition by an observer that the sensor 112 may be reused. In some examples, the adhesive 110 may have different adhesive strength in different regions. For example, an adhesive strength in a region that may be detached from a user responsive to the removal force (e.g., an area generally outside of the circular contour shown in FIG. 1) may have a smaller adhesive strength than a region that may remain attached to the user responsive to the removal force (e.g., an area generally inside the circular contour shown in FIG. 1). Different adhesives and/or different thicknesses of a same adhesive may be used in the different areas in some examples.

Weakened portion 124 may at least partially define two portions of the substrate 102. One portion (e.g., an area outside of the circular contour shown in FIG. 1) may remain attached to weakened portion 126 responsive to a removal force, and in some examples may be wholly and/or partially removed from a user responsive to the removal force. Another portion (e.g., an area at and/or inside of the circular contour shown in FIG. 1) may detach from adhesive 110 responsive to the removal force, and/or may remain attached to the user responsive to the removal force. This may facilitate exposing the sensor 112 to an observer, to allow for more ready recognition that the sensor 112 is reusable.

Weakened portions described herein, including weakened portion 124 and 126 of FIG. 1, may be formed in a variety of ways. For example, a portion of the substrate 102 may be cut, for example, in a perforated line, to form weakened portion 124. In some examples, only a portion of a thickness of substrate 102 (e.g., all or a portion of a thickness of layer 108) may be cut to implement a perforated line in a circular shape shown in FIG. 1. The weakened portion 126 may be formed by cutting a portion of the adhesive 110 to form a perforated line in the partially circular shape shown in FIG. 1. In some examples, an entire thickness of the adhesive 110 may be cut to provide the perforated line. In some examples, a perforated line forming weakened portion 124 and a perforated line forming weakened portion 126 may be positioned such that the cut portions of the perforated lines are positioned at overlapping intervals in plan view.

In some examples, as shown in FIG. 1, the weakened portion 126 and weakened portion 124 may be shaped such that they may fracture in a same direction as the opening and/or closing of lid 120. In other examples, however, the weakened portion 124 and/or weakened portion 126 may be shaped to fracture in a different direction from the opening and/or closing of lid 120.

In some examples, a color of the substrate 102 and/or the adhesive 110 may be different at the weakened portion 124 and/or weakened portion 126, or in the vicinity of the weakened regions. For example, a different color may be used to visually indicate the presence of weakened portion 124 and/or weakened portion 126.

Figure 2:
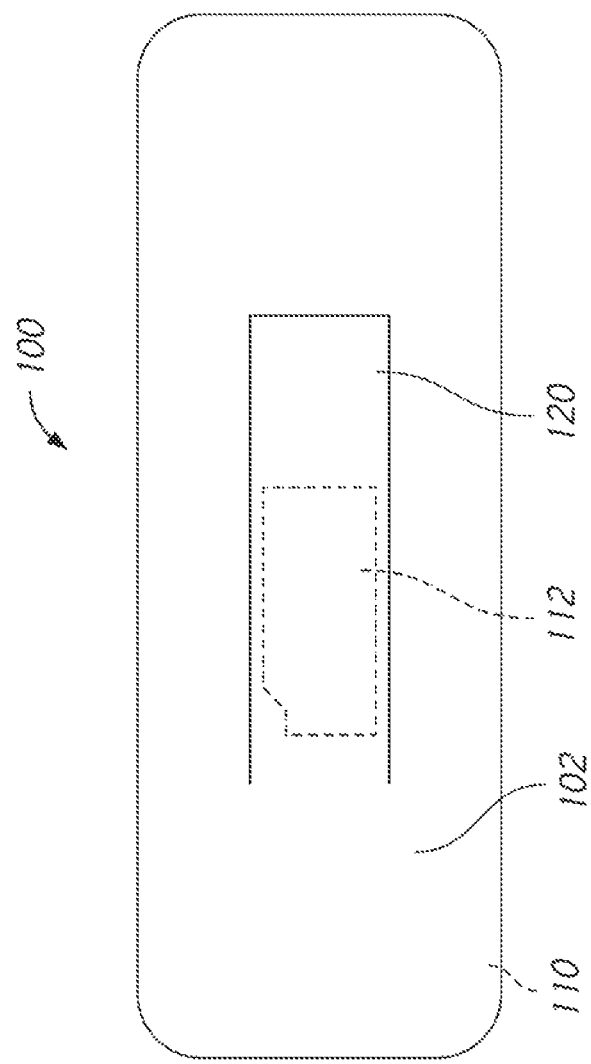
FIG. 2 is a schematic illustration of a plan view of the sensor device of FIG. 1 arranged in accordance with examples described herein.

FIG. 2 is a schematic illustration of a plan view of the sensor device of FIG. 1 arranged in accordance with examples described herein. The surface shown in FIG. 2 may be referred to as a top or front surface of the sensor device 100, while an opposite surface may be referred to as a bottom or back surface of the sensor device 100.

FIG. 2 illustrates a front surface of substrate 102. The adhesive 110 may be positioned beneath the substrate 102, as illustrated using dotted lines in FIG. 2. The lid 120 is shown in FIG. 2, and the sensor 112 may be positioned beneath the lid 120, as illustrated using dotted lines in FIG. 2. The sensor 112 may have an area that is smaller than an area of the lid 120 in some examples, such that the sensor 112 may be positioned within a footprint of the lid 120.

Figure 3:
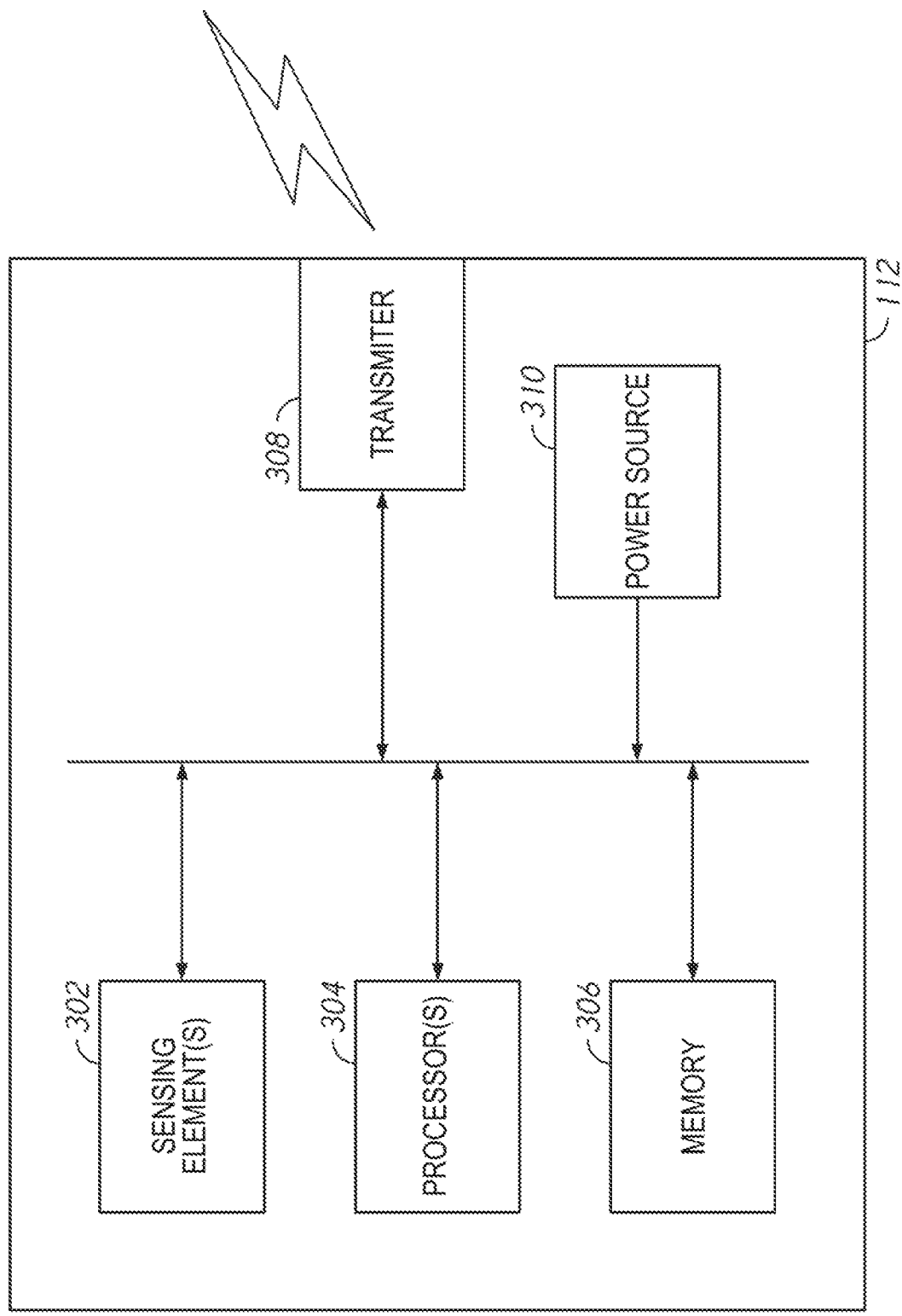
FIG. 3 is a schematic illustration of a sensor arranged in accordance with examples described herein.

FIG. 3 is a schematic illustration of a sensor arranged in accordance with examples described herein. The sensor 112 may be used to implement the sensor 112 of FIG. 1, for example. The sensor 112 includes sensing element(s) 302, processor(s) 304, memory 306, transmitter 308, and power source 310. Additional, fewer, and/or different components may be used in other examples. Generally, a sensor described herein may refer to a reusable portion of a sensor device (e.g., a chip, an SD card, a printed circuit board, packaged circuitry, or combinations thereof). The sensor may generally include electronics for acquiring, processing, and/or analyzing a parameter of a user (e.g., a biopotential signal acquired from a user and/or from an environment of the user).

Sensors described herein may include one or more sensing elements, such as sensing element(s) 302 of FIG. 3. The sensing elements may be implemented generally using any structure for sensing a parameter of a user, including a biological signal or a signal from an environment of the user. The sensing element(s) 302 generally provide signals regarding a parameter of a user (e.g., a biological parameter and/or an environmental parameter). Examples include electrodes. For example, sensing element(s) 302 may be implemented using electrodes which may be electrically connected to electrodes that are placed in contact with a surface of a user during use (e.g. electrodes in adhesive 110 and electrically connected to sensing element(s) 302 using connector 116). In some examples sensing element(s) 302 may be implemented using a pH sensor, temperature sensor, humidity sensor, capacitive sensor, optical sensor, positional sensor (e.g., accelerometer, gyroscope, GPS sensor), or combinations thereof. Any number of sensing elements may be provided in sensor 112, including 1, 2, 3, 4, 5, 6, 7, 8, 9, or 10 sensing elements in some examples. In some examples, sensing elements may be provided in other portions of a sensor device described herein and the sensing element(s) 302 may be implemented using one or more electrodes and/or receivers to receive signals collected by the sensing devices (e.g., through connector 116). In some examples, sensing elements may be positioned in the substrate of a sensor device (e.g., in adhesive 110) and in a reusable portion of the sensor device (e.g., in sensor 112). For example, a biological parameter sensor (e.g., an electrocardiogram sensor) may be provided in a substrate of the sensor device (e.g., in substrate 102 and/or adhesive 110), while an environmental sensor (e.g., an accelerometer) may be provided in the reusable portion of the sensor (e.g., on sensor 112).

Examples of biological parameters of a user which may be collected using sensors and/or sensor devices described herein, include, but are not limited to, body temperature, electrocardiogram, heart rate, impedance respiration, thermistor respiration, pulse, arterial oxygen saturation, blood glucose level, cardiac output, brain waves, electromyogram, or combinations thereof.

Examples of environmental parameters of a user (e.g., parameters relating to an environment in which the user is positioned) include but are not limited to acceleration, positional information, atmospheric pressure, ambient temperature, ambient humidity, noise, ambient illumination, or combinations thereof.

As an example of measurements which may be made by the sensing element(s) 302, in some examples, a geographic position of the user at the time of starting measurement of an electrocardiogram may be reported in a measurement result by the sensing element(s) 302. The ambient temperature and acceleration of the sensor 112 at the time of starting measurement of an electrocardiogram may additionally be reported in a measurement result by the sensing element(s) 302. Information of a geographic position of the user at the time of ending the measurement of the electrocardiogram and the ambient temperature and acceleration of the sensor device at the time of ending the measurement of an electrocardiogram may additionally be reported in a measurement result by the sensing element(s) 302, together with the electrocardiogram data. When variation in acceleration is large, the sensing element(s) 302 and/or the processor(s) 304 may detect the possibility that the user has fallen and report a suspected fall event as a measurement result.

Measurement results generated by the sensing element(s) 302 may be provided to the processor(s) 304 and/or memory 306, e.g., using a wired connection (e.g., one or more conductive lines and/or a bus).

Sensors described herein may include one or more processors, such as processor(s) 304 of FIG. 3. The processor(s) 304 may be implemented, using one or more processors and/or circuitry for performing a processing function, such as logic, application-specific integrated circuits (ASICs), field programmable gate arrays (FPGAs), or combinations thereof. The processor(s) 304 may process signals provided from the sensing element(s) 302 to provide an analysis result. The processor(s) 304 may be provided signals from one or more sensing element(s) 302 and may process, combine, analyze, and/or otherwise manipulate the signals to provide analysis result(s). In some examples, the processor(s) 304 may not be present and/or may not be used, and signals received directly from sensing elements (e.g., sensing element(s) 302) may be stored and/or transmitted.

Sensors described herein may include one or more storage elements, such as memory 306 of FIG. 3. The memory 306 may store one or more measurement signals received from sensing element(s) 302 and/or one or more analysis signals received from processor(s) 304. The memory 306 may be coupled to the sensing element(s) 302 and/or memory 306 using a wired connection (e.g., one or more conductive lines and/or a bus). The memory 306 may be implemented using generally any size, kind, or variety of memory, including read only memory (ROM), random access memory (RAM), flash, solid state memory, or combinations thereof.

Sensors described herein may include one or more transmitters, such as transmitter 308 of FIG. 3. The transmitter 308 may provide one or more measurement signal(s) and/or analysis signal(s), e.g. provided from the sensing element(s) 302, processor(s) 304, and/or memory 306, to a remote device. In some examples, the transmitter 308 may be implemented using one or more output electrodes (e.g., output pads) which may be in electronic communication with other portions of a sensor device described herein, such as antenna 118 of FIG. 1. In some examples, the transmitter 308 may implement all or portions of a wireless communication interface (e.g., a radio) which may provide transmissions in accordance with any wireless protocol (e.g., Wi-Fi, Bluetooth, ZigBee). In some examples, all or portions of the wireless communication interface may be provided in other portions of a sensor device (e.g., in or on substrate 102 and in communication with antenna 118 of FIG. 1). The wireless communication interface may be coupled to a transmitter of the sensor (e.g., through connector 116 of FIG. 1). In this manner, the transmitter 308 may function to provide measurement results, analysis results, or combinations thereof, to one or more remote devices. The transmission may be made directly from transmitter 308 to a remote device, or may be made through other components (e.g., antenna 118 of FIG. 1). In some examples, the transmitter 308 may not be used and/or may not be present. For example, the sensor 112 may be removed from a sensor device described herein when a measurement period is over, and the sensor 112 may be placed in electrical communication with a remote device (e.g., another computer, mobile phone, tablet, server, etc.). The sensor 112 may, for example, be connected to the remote device by inserting the sensor 112 into the remote device and/or attaching a connector between the remote device and the sensor 112. In some examples, wireless communication may be established between the sensor 112 and the remote device when the sensor 112 is removed from the sensor device.

Sensors described herein may include one or more power sources, such as power source 310 of FIG. 3. The power source 310 may provide all or portions of the power used by sensing element(s) 302, processor(s) 304, memory 306, and/or other components of sensor devices described herein. The power source 310 may be implemented using one or more batteries, and/or energy harvesting circuitry. In some examples, the power source 310 may not be present and/or may not be used. For example, components of the sensor 112 may be powered by an external source (e.g., power source 122 of FIG. 1).

Accordingly, during operation, parameters of a user (e.g., biological parameters and/or environmental parameters) may be sensed by sensing elements in a sensor device (e.g., sensing elements in the disposable substrate and/or sensing elements in the reusable sensor). signals from the sensing elements may be provided to the reusable sensor (e.g., using sensing element(s) 302). Measurement result signals from the sensing elements may be provided to processor(s) 304, memory 306, and/or transmitter 308. The processor(s) 304 may process the measurement signal(s) to provide analysis signal(s). The analysis signal(s) may be provided to memory 306 and/or transmitter 308. The transmitter 308 may provide results from sensing element(s) 302, processor(s) 304, and/ or memory 306 to a remote device (e.g., using an antenna). The transmitted signal may be further processed, displayed, and/or analyzed by the remote device. For example, the sensor device may collect an electrocardiogram, which may be reviewed at the remote device for indicators of abnormalities and/or disease (e.g., heart disease).

Figure 4:
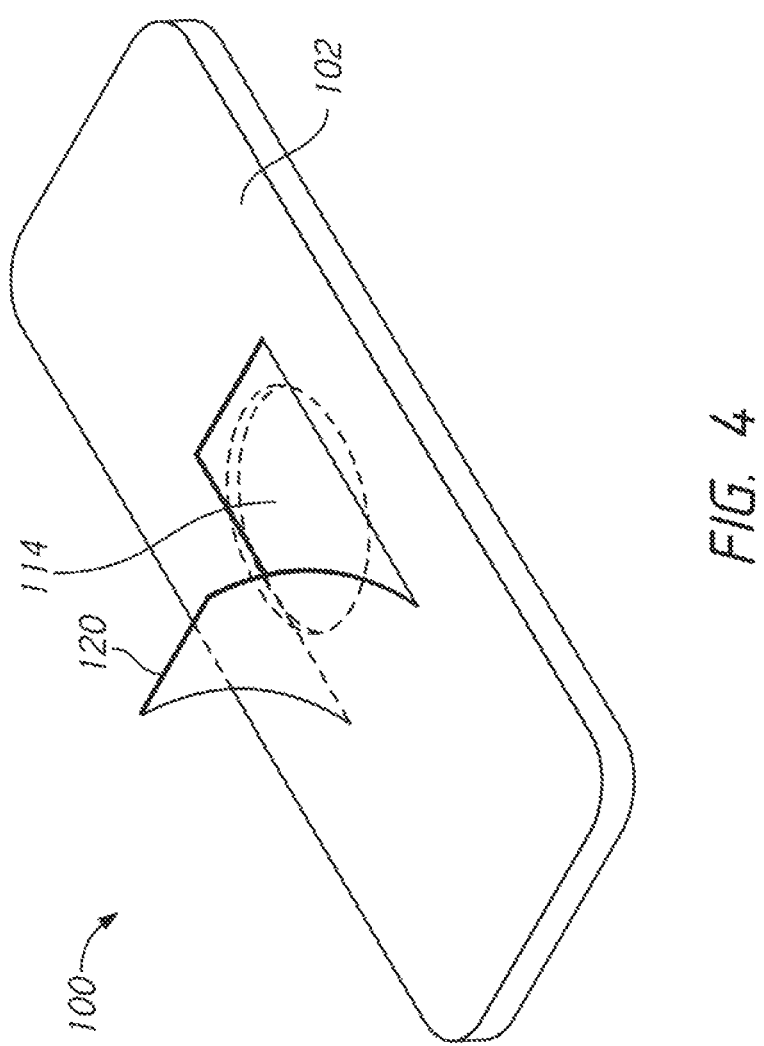
FIG. 4 is a schematic illustration of the sensor device of FIG. 1 before connection with sensor 112, arranged in accordance with examples described herein.

FIG. 4 is a schematic illustration of the sensor device 100 of FIG. 1 before connection with sensor 112, arranged in accordance with examples described herein. To prepare to connect the sensor 112, the lid 120 may be lifted to distance the lid 120 from the substrate 102. The lid 120 may be lifted in a direction away from adhesive 110 (e.g., away from a user). Lifting the lid 120 may expose housing 114 and/or connector 116 in some examples. An observer may now access the connector 116 for insertion of sensor 112.

Figure 5:
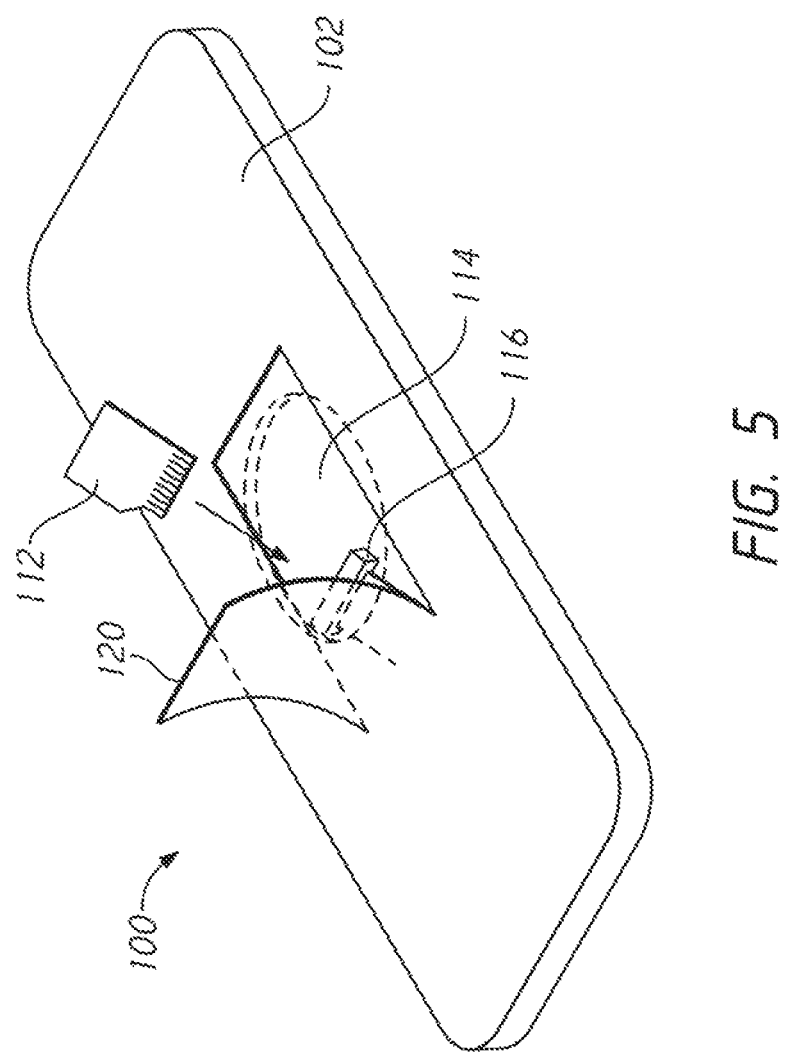
FIG. 5 is a schematic illustration of the sensor device of FIG. 1 during connection with sensor 112, arranged in accordance with examples described herein.

FIG. 5 is a schematic illustration of the sensor device of FIG. 1 during connection with sensor 112, arranged in accordance with examples described herein. After lifting lid 120 to expose housing 114 and/or connector 116, the sensor 112 may be inserted into connector 116. As shown in FIG. 5, for example, an edge of the sensor 112 containing electrical connectors (e.g., electrodes and/or pads), may be inserted into connector 116 which may include mating electrical connectors to establish communication between the sensor device 100 and the sensor 112. Once connected to the connector 116, the sensor 112 may be positioned within the housing 114.

The lid 120 may be returned to a position covering sensor 112. For example, the lid 120 may be moved in a direction toward the sensor 112 (e.g., toward adhesive 110 and/or toward the user). The lid 120 may be closed, e.g., by pressing or otherwise attaching the lid 120 to the substrate 102.

Figure 6:
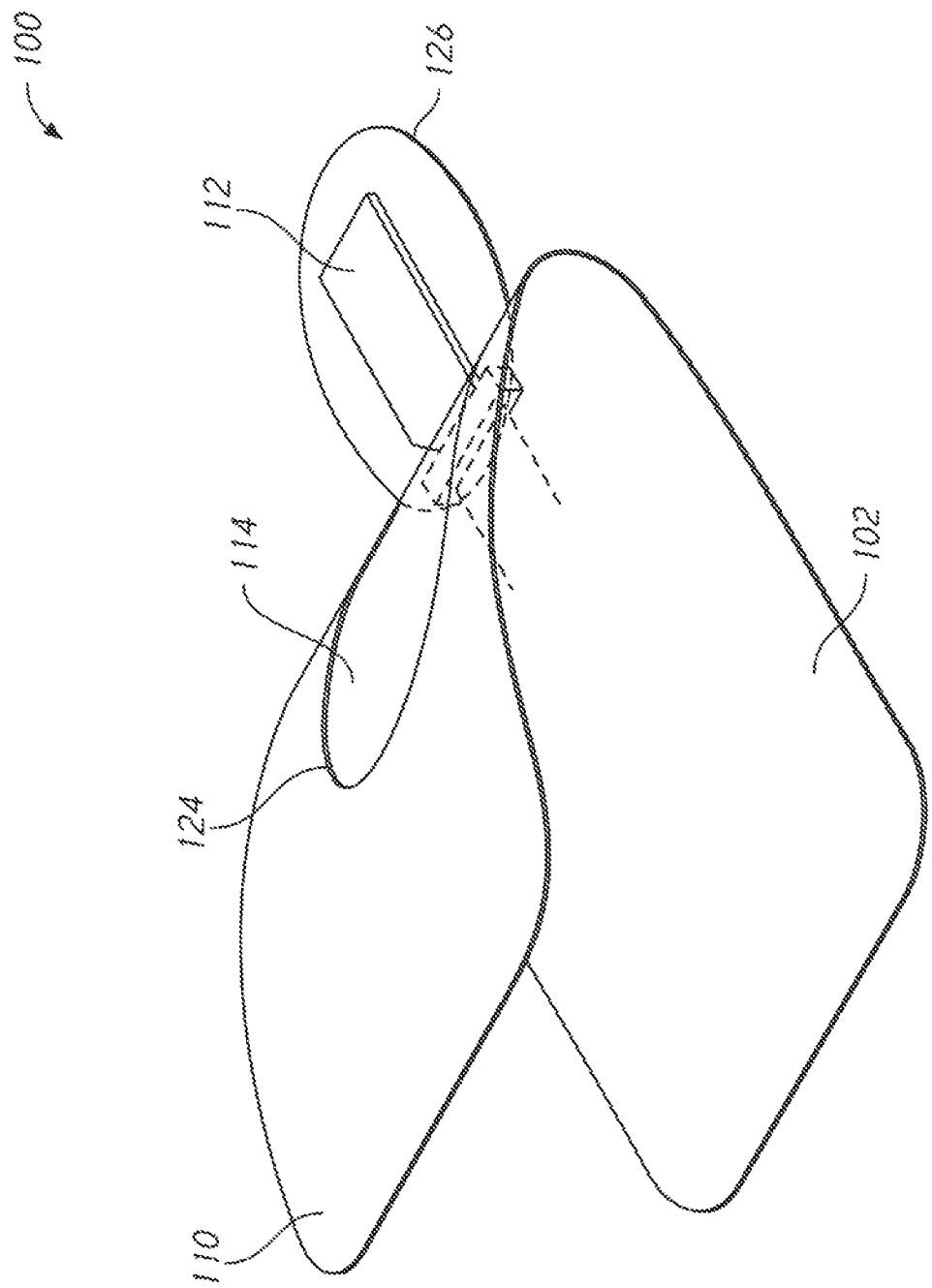
FIG. 6 is a schematic illustration of the sensor device of FIG. 1 during removal of the sensor device from a user.

FIG. 6 is a schematic illustration of the sensor device of FIG. 1 during removal of the sensor device from a user. To remove the sensor device 100 from the user, a removal force may be applied to the substrate 102. For example, the substrate 102 may be peeled off by pulling one end (e.g., edge) of the substrate 102 using, for example, a claw or a hand of an observer or other user. Accordingly, the removal force may be a tensile force pulling the substrate 102 of the sensor device 100 away from the user. An adhesive force of adhesive 110 may oppose the tensile force provided by the removal force. Accordingly, when an applied force is less than the adhesive force, the substrate 102 may remain attached to the user. To remove the sensor device 100, the removal force should be sufficiently large to overcome the adhesive force of the adhesive 110 and begin to remove the substrate 102 from the user.

The weakened portion 124 and weakened portion 126 fracture responsive to a removal force, which may separate the substrate 102 and the adhesive 110 at weakened portion 124 and may separate a portion of the adhesive 110 at weakened portion 126. For example, perforated lines forming the weakened portion 124 and/or weakened portion 126 may fracture (e.g., separate) responsive to the removal force.

Responsive to the removal force, as shown in FIG. 6, part of the sensor device 100 (e.g., approximately half in FIG. 6) may be peeled off from the user. Due in part to the fracturing of the weakened portions, the housing 114 may be opened and the sensor 112 may be exposed. The sensor 112 may be positioned on a body surface of the user, separated by a remaining portion of adhesive 110 and/or substrate 102. The remaining portions may have been defined at least partially by the weakened portion 124 and/or weakened portion 126.

In this manner, an observer (e.g., a nurse, doctor, patient, medical professional), may visually observe an exposed reusable portion of the sensor device 100 (e.g., sensor 112). This may facilitate recognition that the reusable portion may be reused, and may prompt the observe to collect the reusable portion (e.g., disconnect sensor 112 from sensor device 100) for reuse. The sensor 112 may be reused, for example, by connecting the sensor 112 to another sensor device. In some examples, the sensor 112 may be altered prior to connection to another sensor device (e.g., all or portions of a memory included in sensor 112 may be loaded with different information and/or deleted).

Accordingly, methods for using sensor devices described herein may be provided which include removing the sensor device in a manner which exposes a reusable portion of the sensor device (e.g., a sensor, such as sensor 112).

A sensor device may be adhered to a user (e.g., a patient). For example, the sensor device 100 of FIG. 1 may be adhered to a user using adhesive 110. The sensor device may be adhered to generally any surface of user, including a skin surface (e.g., chest, finger, toe, ankle, wrist, arm, leg, back, forehead). The sensor device may be adhered to the user, for example, by pressing the device against a surface of the user such that the adhesive contacts the surface of the user.

At least one parameter of the user (e.g., patient) may be measured with the sensor device. Examples of parameters which may be measured are described herein, for example, with reference to FIG. 3. The parameters (e.g., measurement results, analysis results, or combinations thereof) may be transmitted from the sensor device 100 to one or more remote devices during operation.

To remove the sensor device, a removal force may be applied to the sensor device. For example, a peeling force may be applied to peel a portion of the substrate 102 away from the user. The removal force may fracture the sensor device at weakened portions of the sensor device and, remove at least a portion of the sensor device from the patient. In removing the portion of the sensor device from the patient, a reusable portion of the sensor device (e.g., sensor 112) may be exposed. For example, the reusable portion of the sensor device may remain adhered to the user.

Once exposed, the reusable portion of the sensor device may be recovered. For example, the reusable portion of the sensor device (e.g., sensor 112) may be disconnected from the sensor device. A remaining portion of the sensor device may be removed from the user through application of another removal force, which may in some examples be greater than the first removal force used to remove the first portion of the sensor device from the user.

The reusable portion may be connected to another sensor device in some examples for reuse.

Figure 7:
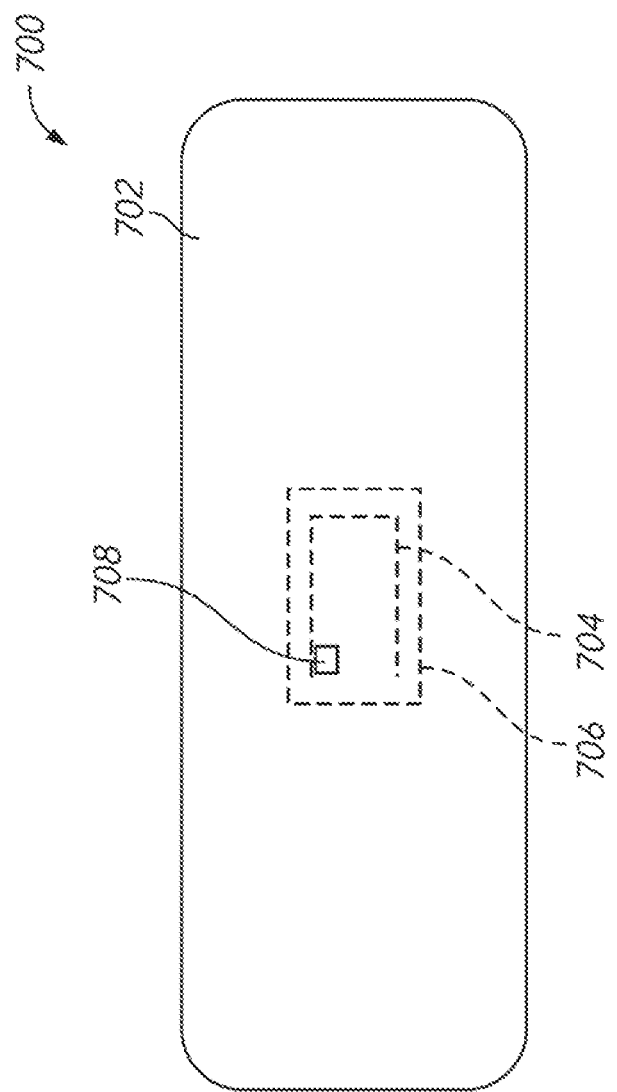
FIG. 7 is a schematic illustration of a plan view of a sensor device arranged in accordance with examples described herein.

FIG. 7 is a schematic illustration of a bottom view of a sensor device arranged in accordance with examples described herein. The sensor device 700 includes adhesive 702, weakened portions 704, housing 706, and sensor 708. Additional, fewer, and/or different components may be used in other examples. A substrate may be present (though not labeled) in FIG. 7.

The example of FIG. 7 illustrates an example sensor device 700 which may have components analogous to the sensor device 100 of FIG. 1, but which utilizes a housing having a rectangular shape. Accordingly, housing 706 has a rectangular shape, which may house a rectangular reusable portion (e.g., sensor 708).

The weakened portions 704 may correspond with three sides of a rectangular shape of a housing 706. The weakened portions 704 may include a weakened portion formed in a substrate of the sensor device 700 and a weakened portion formed in adhesive 702. As described herein, the weakened portions may be formed, for example, using perforated lines.

The sensor 708, or a portion of the sensor 708, and/or a component of the sensor device 700 in communication with the sensor 708 may be exposed to a user during operation for measurement of a parameter of a user. For example, the sensor 708 may be implemented using a temperature sensor in some examples.

To remove the sensor device 700 from a user, a short side of the sensor device 700 (e.g., on the right side of FIG. 7, toward a short end of the partial rectangle defined by weakened portions 704) The side of weakened portions 704 closest to the side of the sensor device 700 which is being pulled may be fractured first. When the sensor device 700 is further pulled, the two adjacent sides of the weakened portions 704 may be fractured. Fracturing the weakened portions 704 may expose housing 706 and/or sensor 708.

Figure 8:
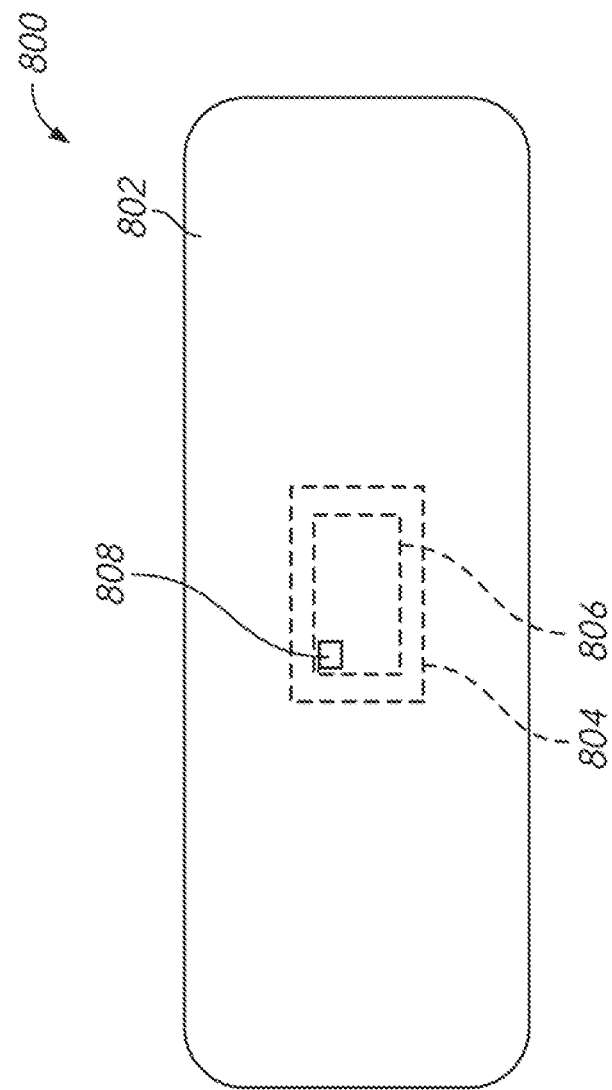
FIG. 8 is a schematic illustration of a plan view of a sensor device arranged in accordance with examples described herein.

FIG. 8 is a schematic illustration of a plan view of a sensor device arranged in accordance with examples described herein. The sensor device 800 includes adhesive 802, housing 804, weakened portions 806, and sensor 808. Additional, fewer, and/or different components may be used in other examples. A substrate may be present (though not labeled) in FIG. 8.

The example of FIG. 8 illustrates an example sensor device 800 which may have components analogous to the sensor device 100 of FIG. 1, but which utilizes a housing having a rectangular shape, similar to the sensor device 700 of FIG. 7. However, the sensor device 800 of FIG. 8 includes weakened portions 806 which may be formed in a shape of a complete rectangle. Accordingly, housing 804 has a rectangular shape, which may house a rectangular reusable portion (e.g., sensor 808).

The weakened portions 806 may be formed in the adhesive 802 of the sensor device 800, a substrate of the sensor device 800, or both.

When the sensor device 800 is pulled such that the substrate and/or adhesive 802 pulls back a position generally overlapping with part of the weakened portions 806 a side of the weakened portions 806 close to the portion of the sensor device 800 being pulled back may fracture. When the sensor device 800 is further pulled, two sides of the housing 804 adjacent to the initial fracture side may also be fractured. When the sensor device 800 is further pulled, the weakened portions 806 may be completely fractured, and an area defined by the weakened portions 806 (including, for example housing 804) may be exposed, and it may be apparent that sensor 808 may be reused.

The example of FIG. 8 illustrates an example sensor device 800 which may have components analogous to the sensor device 100 of FIG. 1, but which utilizes a housing having a rectangular shape, similar to the sensor device 700 of FIG. 7. Accordingly, housing 706 has a rectangular shape, which may house a rectangular reusable portion (e.g., sensor 708).

Figure 9:
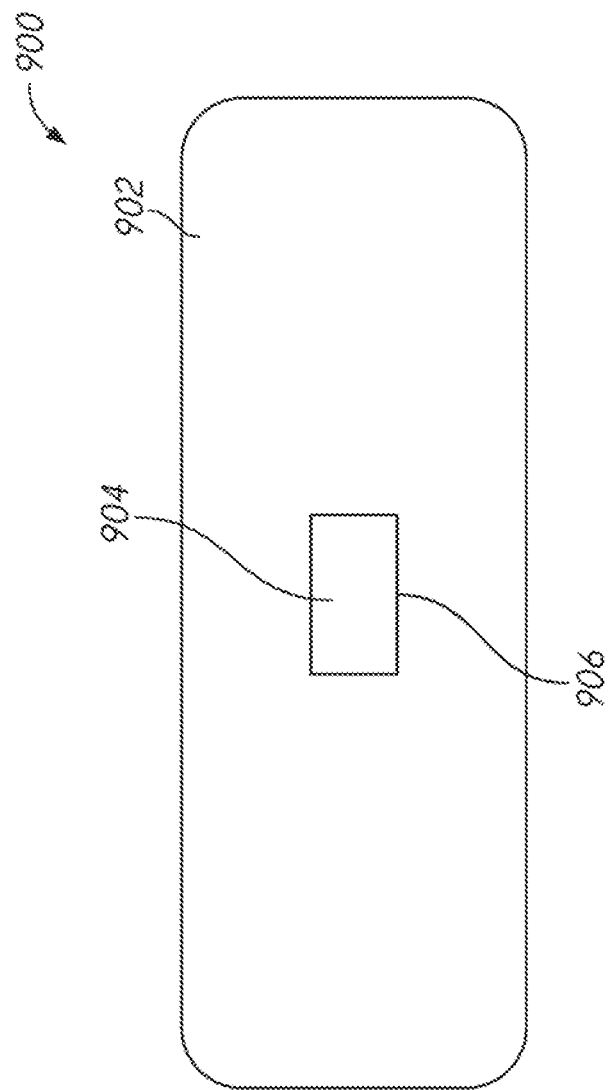
FIG. 9 is a schematic illustration of a plan view of a sensor device arranged in accordance with examples described herein.

FIG. 9 is a schematic illustration of a plan view of a sensor device arranged in accordance with examples described herein. The sensor device 900 includes first area 902, second area 904, and weakened portion 906. Additional, fewer and/or different components may be provided in other examples. A substrate may be present (though not labeled) in FIG. 9. FIG. 9 illustrates a plan view of a bottom side (e.g., adhesive side) of sensor device 900.

The example of FIG. 9 illustrates an example sensor device 900 which may have components analogous to the sensor device 100 of FIG. 1, and the sensor device 800 of FIG. 8, but where the weakened portion 906 may be formed by an intersection of adhesive areas having different adhesive strengths.

The weakened portion 906 provided in an adhesive of the sensor device 900 may be formed by varying the strength of the adhesive force. Generally, the adhesive in the second area 904 may be stronger than the adhesive in the first area 902. In this manner, an intersection between the two may form the weakened portion 906. For example, a boundary between first area 902 and second area 904 may define weakened portion 906.

When the sensor device 900 is pulled and peeled off (e.g., after a measurement period), the weakened portion 906 formed by a boundary portion between the first area 902 and second area 904 may be fractured as the adhesive force of the second area 904 is higher than the adhesive force of the first area 902.

When the weakened portion 906 is fractured, a reusable portion of the sensor device 900 may be exposed, as described herein. Accordingly, the reusable portion (e.g., a sensor) may be readily visible by an observer.

Generally, weakened portions described herein, such as weakened portion 124, weakened portion 126, weakened portions 704, weakened portions 806, and/or weakened portion 906, may have various structures. In some examples, the weakened portions may be formed using one or more perforated lines. In some examples, the weakened portions may be formed by a boundary between two different strength adhesives. In some examples, the weakened portions may have a color which may be different than a color of another portion of the substrate adhesive, and/or sensor device For example, a color of the weakened portions may be different than a color of an adjacent portion of the substrate, adhesive, and/or sensor device.

The color of the weakened portions may be a color which may not be normally used for a sensor device, for example, various fluorescent colors or a red color used for warning or danger can be used.

In this manner, contours of the weakened portions may be conspicuous with respect to colors of the common sensor device (e.g., colors close to colors of the body surface of the user, for example, may be flesh color, milk white, white etc.). This may aid an observe in readily recognizing fracture of the weakened portions and/or presence of a reusable portion of the sensor device (e.g., a sensor described herein).

Figure 10:
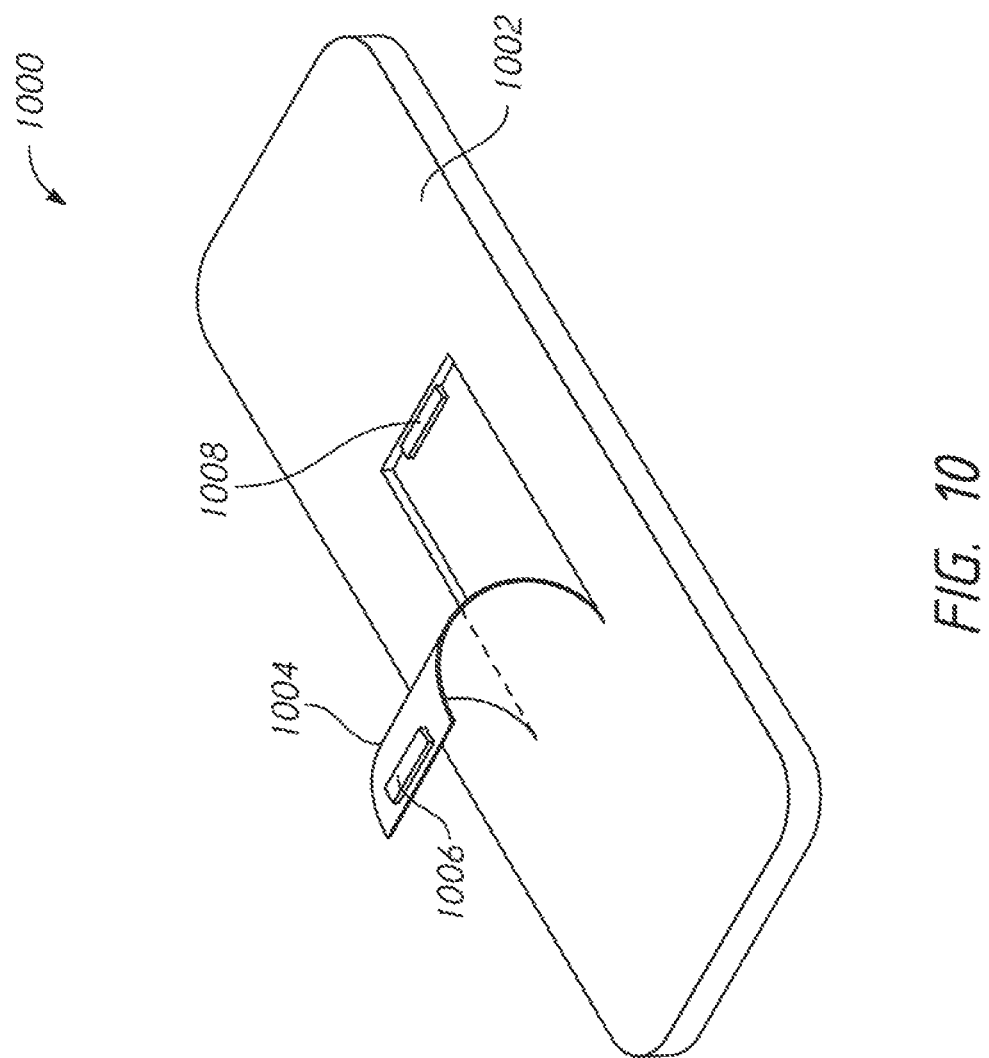
FIG. 10 is a schematic illustration of a plan view of a sensor device arranged in accordance with examples described herein.

FIG. 10 is a schematic illustration of a plan view of a sensor device arranged in accordance with examples described herein. The sensor device 1000 includes substrate 1002, lid 1004, closure 1006, and closure 1008. Additional, fewer and/or different components may be provided in other examples. FIG. 10 illustrates a plan view of a top side of sensor device 1000.

The example of FIG. 10 illustrates an example sensor device 1000 which may have components analogous to the sensor device 100 of FIG. 1, or other sensor devices described herein, but where the lid 1004 may have closure features.

Lid 1004 may at least partially enclose a reusable portion of the sensor device 1000 within a housing by closing the lid 1004. A reusable portion (e.g., a sensor) may be more securely held in a housing described herein when a lid is closed over the housing and may even more securely be held when the lid is secured to the sensor device 1000 (e.g., using securing features).

Accordingly, the lid 1004 may include closure 1006 on a back surface of the lid 1004 that contacts the sensor device 1000 when the lid 1004 is pressed onto a surface of the sensor device 1000, for example onto a surface of a substrate of the sensor device. A closure 1008 on the sensor device 1000 (e.g., on a substrate of the sensor device 1000) may bond, connect, adhere, or otherwise mate with the closure 1006 when the lid 1004 is pressed toward the sensor device 1000.

The closure 1006 and/or closure 1008 may form a connection which may be repeatedly attachable and detachable in some examples. In some examples, a connection between closure 1006 and closure 1008 may be permanent. The closure 1006 and closure 1008 may be implemented, for example, using seals, raised structures, mating structures, adhesives, or combinations thereof.

During use, the lid 1004 may be lifted to separate the lid 1004 from a remainder of the sensor device 1000 (e.g., in an upper direction, away from the surface of the sensor device 1000 intended for contact with a surface of a user). Once lifted, a reusable portion of the sensor device 1000 (e.g., a sensor) may be inserted into an exposed housing and/or connector. Once inserted, the closure 1006 and closure 1008 may be connected, for example by pressing the lid 1004 toward the sensor device 1000.

In this manner, once the closure 1006 and closure 1008 are connected, the lid 1004 may not separate from the sensor device 1000 during normal use, even if the sensor device 1000 may be bent or folded in some examples. This may aid in retaining a sensor or other reusable portion within a housing of the sensor device 1000.

The lid 1004 including closure 1006 and closure 1008 may be used to implement any lid described herein, including lid 120 of FIG. 1.

The present invention is not limited to the above embodiments and the modification examples and may be freely modified and improved appropriately. Additionally, the material, the shape, the form, the number, arrangement places and the like of respective components according to the above embodiments are arbitrary and are not limited as long as they can achieve the present invention.

What is claimed is:

1. A sensor device comprising:
    a substrate;
    adhesive positioned to adhere the substrate to a user;
    a sensor configured to measure a parameter of a user, wherein the sensor is supported by the substrate; and
    wherein the substrate, the adhesive, or combinations thereof, include:
        weakened portions configured to fracture responsive to a removal force applied to the sensor device to peel the sensor device off a surface of the user and an adhesive force of the adhesive and expose the sensor, wherein the weakened portions are respectively provided on the substrate and the adhesive, and
        a connecting portion which connects a first portion of the adhesive configured to remain attached to the user following application of the removal force and a second portion of the adhesive configured to detach from the user following application of the removal force,
    wherein the connecting portion is configured to connect the first portion and the second portion of the adhesive before and after the application of the removal force causes the second portion of the adhesive to detach from the user,
    wherein the weakened portions are configured to define a boundary between the first portion of the adhesive and the second portion of the adhesive, and
    wherein the substrate comprises:
        a first layer configured to adhere to the adhesive, wherein the first layer comprises a first weakened portion of the weakened portions and the adhesive comprises a second weakened portion of the weakened portions, and wherein the first weakened portion corresponds to the second weakened portion; and
        a second layer above the first layer, wherein the second layer comprises a housing configured to receive the sensor, and wherein the housing corresponds to the first and second weakened portions.

2. The sensor device according to claim 1, further comprising a housing coupled to the substrate, the housing at least partially enclosing the sensor.

3. The sensor device according to claim 1, wherein the weakened portions are formed at positions corresponding to three sides of a rectangle enclosing the sensor.

4. The sensor device according to claim 1, wherein the first portion of the adhesive corresponds to a first portion of the substrate and the second portion of the adhesive corresponds to a second portion of the substrate, and wherein the adhesive in the first portion of the adhesive has a higher adhesive force than the adhesive in the second portion of the adhesive.

5. The sensor device according to claim 1, wherein the weakened portions comprise at least one perforated line.

6. The sensor device according to claim 1, wherein the weakened portions have a color different than a color of a remaining portion of the substrate.

7. The sensor device according to claim 1, wherein the sensor further comprises at least one processor configured to receive signals from a sensing element and process the signals to provide at least one measurement result.

8. The sensor device according to claim 7, wherein the sensor further comprises a memory configured to store the at least one measurement result.

9. The sensor device according to claim 8, wherein the sensor device further comprises a transmitter configured to transmit the at least one measurement result stored in the memory to a remote device.

10. The sensor device according to claim 1, wherein the weakened portions are located between the first portion of the adhesive configured to remain attached to the user following application of the removal force or a portion of the substrate which is in contact with the first portion of the adhesive, and the second portion of the adhesive configured to detach from the user following application of the removal force or a portion of the substrate which is in contact with the second portion of the adhesive, in in-plane direction of the substrate.

11. A substrate system for a sensor device, the substrate system comprising:
    a substrate;
    a connector at least partially supported by the substrate, the connector configured to receive a sensor, the sensor configured to measure a parameter of a user;
    wherein the substrate includes weakened portions configured to fracture responsive to a removal force and an adhesive force of an adhesive, wherein the removal force is applied to the sensor device to peel the sensor device off a surface of the user,
    wherein the weakened portions are respectively provided on the substrate and the adhesive,
    wherein the weakened portions at least partially define a first portion of the substrate configured to remain attached to the user following application of the removal force and a second portion of the substrate configured to detach from the user following application of the removal force, and
    wherein the substrate, the adhesive, or combinations thereof, further include a connecting portion which connects a first portion of the adhesive configured to remain attached to the user following application of the removal force and a second portion of the adhesive configured to detach from the user following application of the removal force, wherein the connecting portion is configured to connect the first portion of the adhesive and the second portion of the adhesive before and after the application of the removal force causes the second portion of the adhesive to detach from the user, wherein the weakened portions are configured to define a boundary between the first portion of the adhesive and the second portion of the adhesive, and wherein the substrate comprises:
- a first layer configured to adhere to the adhesive, wherein the first layer comprises a first weakened portion of the weakened portions and the adhesive comprises a second weakened portion of the weakened portions, and wherein the first weakened portion corresponds to the second weakened portion; and
- a second layer above the first layer, wherein the second layer comprises a housing configured to receive the sensor, and wherein the housing corresponds to the first and second weakened portions.

12. The sensor device according to claim 11, wherein the weakened portions are formed at positions corresponding to three sides of a rectangle enclosing the connector.

13. The sensor device according to claim 11, wherein the first portion of the adhesive corresponds to the first portion of the substrate and the second portion of the adhesive corresponds to the second portion of the substrate, wherein the adhesive in the first portion of the adhesive has a higher adhesive force than the adhesive in the second portion of the adhesive.

14. The substrate system according to claim 11, wherein the weakened portions are located between the first portion of the adhesive configured to remain attached to the user following application of the removal force or a portion of the substrate which is in contact with the first portion of the adhesive, and the second portion of the adhesive configured to detach from the user following application of the removal force or a portion of the substrate which is in contact with the second portion of the adhesive, in in-plane direction of the substrate.

15. A method comprising:
adhering a sensor device to a patient, wherein the sensor device includes a sensor, a substrate, and weakened portions at least partially defining a first portion of the sensor device and a second portion of the sensor device;
measuring at least one parameter of the patient with the sensor device;
applying a removal force to the sensor device, the removal force configured to fracture the sensor device at the weakened portions and at least partially remove the first portion of the sensor device from a surface of the patient; and
fracturing the sensor device at the weakened portions with the removal force and an adhesive force of an adhesive, wherein the adhesive includes a connecting portion which connects a first portion of the adhesive configured to remain attached to the patient following application of the removal force and a second portion of the adhesive configured to detach from the user following application of the removal force, wherein the connecting portion is configured to connect the first portion of the adhesive and the second portion of the adhesive before and after the application of the removal force causes the second portion of the adhesive to detach from the patient, wherein the weakened portions are respectively provided on the substrate and the adhesive, wherein the weakened portions are configured to define a boundary between the first portion of the adhesive and the second portion of the adhesive, and wherein the substrate comprises:
- a first layer configured to adhere to the adhesive, wherein the first layer comprises a first weakened portion of the weakened portions and the adhesive comprises a second weakened portion of the weakened portions, and wherein the first weakened portion corresponds to the second weakened portion; and
- a second layer above the first layer, wherein the second layer comprises a housing configured to receive the sensor, and wherein the housing corresponds to the first and second weakened portions.

16. The method of claim 15, wherein the removal force is further configured to at least partially remove the first portion of the sensor device from the patient while retaining the second portion of the sensor device adhered to the patient.

17. The method of claim 15, wherein said applying the removal force comprises peeling at least a portion of the sensor device away from the patient.

18. The method of claim 15, wherein said measuring at least one parameter comprises transmitting a signal indicative of the at least one parameter from the sensor device to a remote device.

19. The method of claim 15, wherein the removal force is a first removal force, the method further comprising applying a second removal force to the sensor device, the second removal force configured to remove the second portion of the sensor device from the patient, wherein the second removal force is greater than the first removal force.

20. The method according to claim 15, wherein the weakened portions are located between the first portion of the adhesive configured to remain attached to the user following application of the removal force or a portion of the substrate which is in contact with the first portion of the adhesive, and the second portion of the adhesive configured to detach from the user following application of the removal force or a portion of the substrate which is in contact with the second portion of the adhesive, in in-plane direction of the substrate.

* * * * *